US012564326B2

(12) United States Patent
Kulkarni et al.

(10) Patent No.: US 12,564,326 B2
(45) Date of Patent: Mar. 3, 2026

(54) NON-INVASIVE BILIRUBIN DETECTION USING INDUCED PHOTOREACTION

(71) Applicant: GE Precision Healthcare LLC, Wauwatosa, WI (US)

(72) Inventors: Aditya Kulkarni, Bengaluru (IN); Vamshi Kommareddy, Hyderabad (IN); Prasad Thapa, Bengaluru (IN); Gnanasekar Velusamy, Bengaluru (IN); Venugopal Manoharan, Narasangkuppam (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 332 days.

(21) Appl. No.: 18/488,357

(22) Filed: Oct. 17, 2023

(65) Prior Publication Data

US 2024/0130619 A1    Apr. 25, 2024
US 2024/0225449 A9    Jul. 11, 2024

Related U.S. Application Data

(60) Provisional application No. 63/380,888, filed on Oct. 25, 2022.

(51) Int. Cl.
   *A61B 5/00*      (2006.01)
   *A61B 5/1455*    (2006.01)
(52) U.S. Cl.
   CPC .......... *A61B 5/0059* (2013.01); *A61B 5/1455* (2013.01)

(58) Field of Classification Search
CPC .. A61B 5/1455; A61B 5/14551; A61B 5/0059
See application file for complete search history.

(56) References Cited

U.S. PATENT DOCUMENTS

| | | | |
|---|---|---|---|
| 3,569,721 A | 3/1971 | Goldberg et al. | |
| 3,980,696 A | 9/1976 | Anderson | |
| 4,029,085 A | 6/1977 | Dewitt et al. | |
| 4,571,383 A | 2/1986 | Takayama et al. | |
| 4,806,485 A | 2/1989 | Birks et al. | |
| 5,259,382 A | 11/1993 | Kronberg | |
| 5,262,304 A | 11/1993 | Taniguchi | |
| 5,353,790 A | 10/1994 | Jacques et al. | |
| 5,449,622 A | 9/1995 | Yabe et al. | |
| 5,791,345 A | 8/1998 | Ishihara et al. | |

(Continued)

FOREIGN PATENT DOCUMENTS

| | | |
|---|---|---|
| CN | 2109570 U | 7/1992 |
| CN | 1064152 A | 9/1992 |

(Continued)

OTHER PUBLICATIONS

"Dräger Jaundice Meter JM-105 Jaundice Management", Dräger, 2013, 6 pages.

(Continued)

*Primary Examiner* — Eric F Winakur

(57) ABSTRACT

Techniques are disclosed for measuring a concentration of an analyte in a subject based on reflectance spectra obtained from the subject. The spectra are obtained while and/or before and/or after photoreactions are induced in the subject, where the photoreactions change the reflectivity of the subject. The rate of change of the reflectivity is correlated with the concentration of the analyte.

24 Claims, 10 Drawing Sheets

(56)                References Cited

U.S. PATENT DOCUMENTS

| | | | |
|---|---|---|---|
| 5,792,049 A | 8/1998 | Eppstein et al. | |
| 5,882,301 A | 3/1999 | Yoshida | |
| 5,885,224 A | 3/1999 | Yoshida | |
| 5,910,421 A | 6/1999 | Small et al. | |
| 5,933,226 A | 8/1999 | Yamanishi | |
| 5,983,120 A | 11/1999 | Groner et al. | |
| 6,064,898 A | 5/2000 | Aldrich | |
| 6,087,182 A | 7/2000 | Jeng et al. | |
| 6,477,394 B2 | 11/2002 | Rice et al. | |
| 6,522,398 B2 | 2/2003 | Cadell et al. | |
| 6,553,242 B1 | 4/2003 | Sarussi | |
| 6,596,016 B1 | 7/2003 | Vreman et al. | |
| 6,671,528 B2 | 12/2003 | Steuer et al. | |
| 6,943,883 B2 | 9/2005 | Fodgaard | |
| 6,954,661 B2 | 10/2005 | Cho et al. | |
| 7,039,446 B2 * | 5/2006 | Ruchti | A61B 5/1455 |
| | | | 600/316 |
| 7,171,251 B2 | 1/2007 | Sarussi et al. | |
| 7,760,340 B2 | 7/2010 | Hoshiko et al. | |
| 7,869,033 B2 | 1/2011 | Masilamani et al. | |
| 8,054,452 B2 | 11/2011 | Bado et al. | |
| 8,335,550 B2 | 12/2012 | Segman | |
| 9,173,603 B2 | 11/2015 | Molcho et al. | |
| 9,259,486 B2 | 2/2016 | Koenig | |
| 9,279,763 B2 | 3/2016 | Meijer et al. | |
| 9,366,662 B2 | 6/2016 | Babson | |
| 9,535,053 B1 | 1/2017 | Cafferty et al. | |
| 9,594,076 B2 | 3/2017 | Sass | |
| 9,638,686 B1 | 5/2017 | Cafferty et al. | |
| 9,933,411 B2 | 4/2018 | Cafferty et al. | |
| 10,088,468 B2 | 10/2018 | Cafferty et al. | |
| 10,463,283 B2 | 11/2019 | Ferber et al. | |
| 10,512,657 B2 | 12/2019 | Gedulin et al. | |
| 10,712,347 B2 | 7/2020 | Strano et al. | |
| 10,732,038 B2 | 8/2020 | Cafferty et al. | |
| 2003/0198970 A1 | 10/2003 | Roberts | |
| 2003/0202170 A1 | 10/2003 | Shepherd et al. | |
| 2007/0026393 A1 | 2/2007 | Berlin et al. | |
| 2007/0135335 A1 | 6/2007 | Collier et al. | |
| 2007/0286856 A1 | 12/2007 | Brown et al. | |
| 2008/0311107 A1 | 12/2008 | Bollinger et al. | |
| 2009/0313707 A1 | 12/2009 | Combs et al. | |
| 2012/0313268 A1 | 12/2012 | Bianchi et al. | |
| 2013/0315913 A1 | 11/2013 | Zhang | |
| 2015/0185233 A1 | 7/2015 | Raiker et al. | |
| 2016/0047740 A1 | 2/2016 | Park et al. | |
| 2016/0198992 A1 | 7/2016 | Sandrin et al. | |
| 2017/0032099 A1 | 2/2017 | Cales et al. | |
| 2017/0082603 A1 | 3/2017 | Cales et al. | |
| 2017/0192021 A1 | 7/2017 | Sheppard et al. | |
| 2018/0149635 A1 | 5/2018 | Abir | |
| 2019/0025210 A1 | 1/2019 | Neijzen et al. | |
| 2019/0079063 A1 | 3/2019 | Gilboa-Geffen et al. | |
| 2019/0262629 A1 | 8/2019 | Broer et al. | |
| 2019/0276872 A1 | 9/2019 | Lichte et al. | |
| 2019/0343426 A1 | 11/2019 | Vartdal et al. | |
| 2020/0088744 A1 | 3/2020 | Golmohammadi Ghane et al. | |
| 2020/0163593 A1 | 5/2020 | Trau et al. | |

FOREIGN PATENT DOCUMENTS

| CN | 1158636 A | 9/1997 |
|---|---|---|
| CN | 1074790 C | 11/2001 |
| CN | 101221129 A | 7/2008 |
| CN | 101363869 A | 2/2009 |
| CN | 102107031 A | 6/2011 |
| CN | 101122605 B | 7/2011 |
| CN | 201899488 U | 7/2011 |
| CN | 101319993 B | 11/2011 |
| CN | 102525651 A | 7/2012 |
| CN | 102944683 A | 2/2013 |
| CN | 203303153 U | 11/2013 |
| CN | 103558171 A | 2/2014 |
| CN | 103961803 A | 8/2014 |
| CN | 104548379 A | 4/2015 |
| CN | 103300927 B | 9/2015 |
| CN | 103977772 B | 1/2016 |
| CN | 204931687 U | 1/2016 |
| CN | 105327336 A | 2/2016 |
| CN | 105362765 A | 3/2016 |
| CN | 105980833 A | 9/2016 |
| CN | 106202968 A | 12/2016 |
| CN | 205759157 U | 12/2016 |
| CN | 106295148 A | 1/2017 |
| CN | 107115593 A | 9/2017 |
| CN | 206534620 U | 10/2017 |
| CN | 206627519 U | 11/2017 |
| CN | 107951924 A | 4/2018 |
| CN | 107966410 A | 4/2018 |
| CN | 207232812 U | 4/2018 |
| CN | 108208266 A | 6/2018 |
| CN | 207623224 U | 7/2018 |
| CN | 104395729 B | 8/2018 |
| CN | 108615214 A | 10/2018 |
| CN | 109171757 A | 1/2019 |
| CN | 208448445 U | 2/2019 |
| CN | 109789312 A | 5/2019 |
| CN | 109925472 A | 6/2019 |
| CN | 109952099 A | 6/2019 |
| CN | 110192865 A | 9/2019 |
| CN | 110279699 A | 9/2019 |
| CN | 110621673 A | 12/2019 |
| CN | 110652413 A | 1/2020 |
| CN | 110711278 A | 1/2020 |
| CN | 110823880 A | 2/2020 |
| CN | 111004866 A | 4/2020 |
| CN | 111093494 A | 5/2020 |
| DE | 102017008631 A1 | 4/2018 |
| EP | 0071650 A1 | 2/1983 |
| EP | 0175330 B1 | 11/1991 |
| EP | 0679064 A1 | 11/1995 |
| EP | 0747002 A1 | 12/1996 |
| EP | 1169294 A2 | 1/2002 |
| EP | 1278452 A1 | 1/2003 |
| EP | 2458384 A2 | 5/2012 |
| EP | 2968230 A2 | 1/2016 |
| EP | 3296720 A1 | 3/2018 |
| EP | 3296739 A1 | 3/2018 |
| EP | 3377877 A1 | 9/2018 |
| EP | 3411689 A1 | 12/2018 |
| EP | 3438841 A1 | 2/2019 |
| EP | 3470839 A1 | 4/2019 |
| EP | 3513193 A1 | 7/2019 |
| EP | 3544504 A1 | 10/2019 |
| EP | 3591378 A1 | 1/2020 |
| EP | 3302449 B1 | 4/2020 |
| GB | 1250218 A | 10/1971 |
| GB | 1335483 A | 10/1973 |
| GB | 2046901 A | 11/1980 |
| GB | 2406638 A | 4/2005 |
| WO | 9639927 A1 | 12/1996 |
| WO | 9964627 A2 | 12/1999 |
| WO | 2005003351 A1 | 1/2005 |
| WO | 2005014634 A1 | 2/2005 |
| WO | 2009101538 A2 | 8/2009 |
| WO | 2012038930 A1 | 3/2012 |
| WO | 2013068518 A1 | 5/2013 |
| WO | 2014049131 A1 | 4/2014 |
| WO | 2016159050 A1 | 10/2016 |
| WO | 2016179981 A1 | 11/2016 |
| WO | 2017017676 A1 | 2/2017 |
| WO | 2017167030 A1 | 10/2017 |
| WO | 2019089768 A1 | 5/2019 |
| WO | 2019126470 A1 | 6/2019 |
| WO | 2019090158 A9 | 8/2019 |
| WO | 2019206929 A2 | 10/2019 |
| WO | 2020031196 A1 | 2/2020 |
| WO | 2020036565 A2 | 2/2020 |
| WO | 2020145899 A1 | 7/2020 |

OTHER PUBLICATIONS

"Quick Reults With a Simple Touch—Philips Bilichek Noninvasive

(56) References Cited

OTHER PUBLICATIONS

Bilirubin Assessment Tool", Philips; Mother & Child Care; Jaundice Management, 2017, 8 Pages.

\* cited by examiner

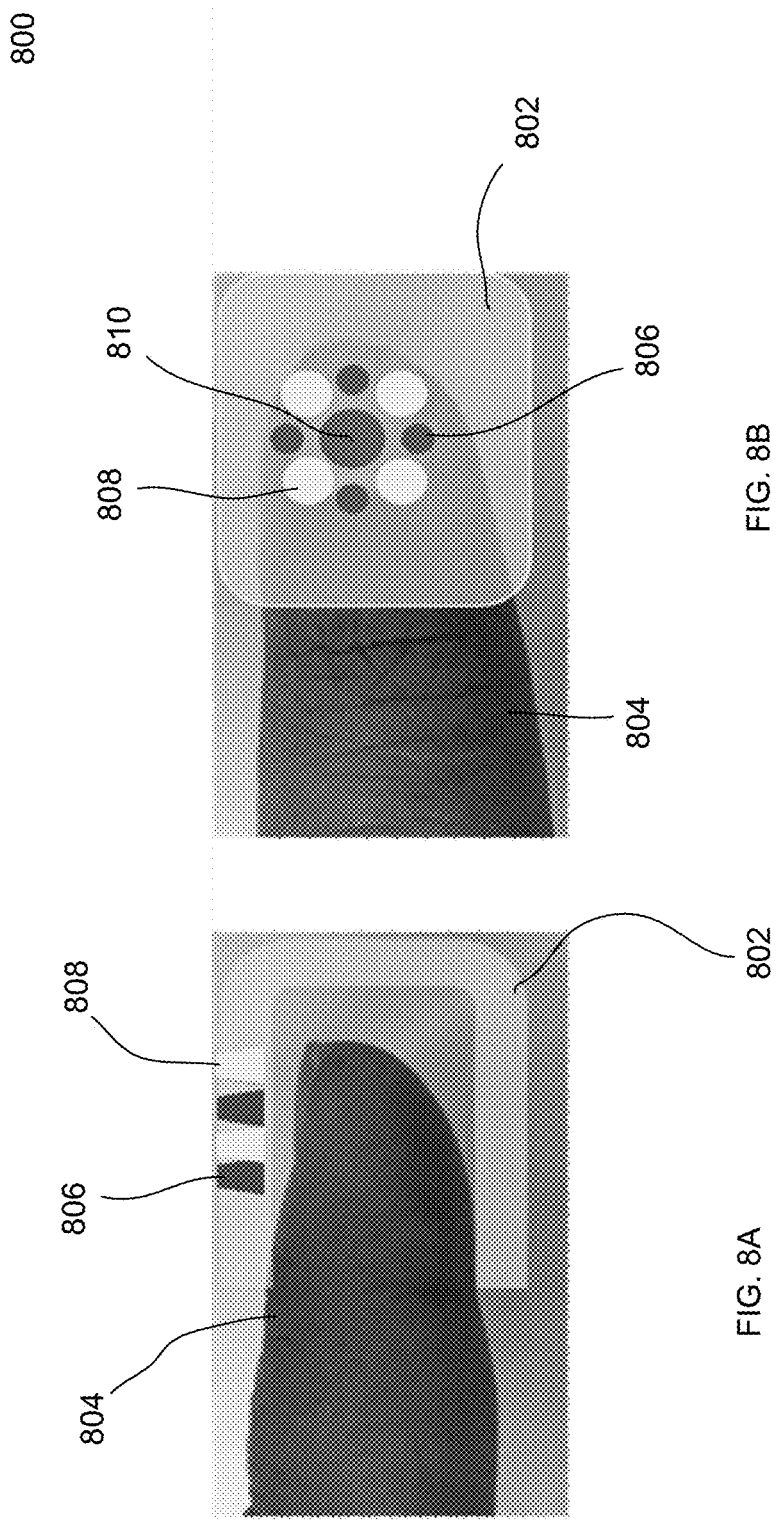

900

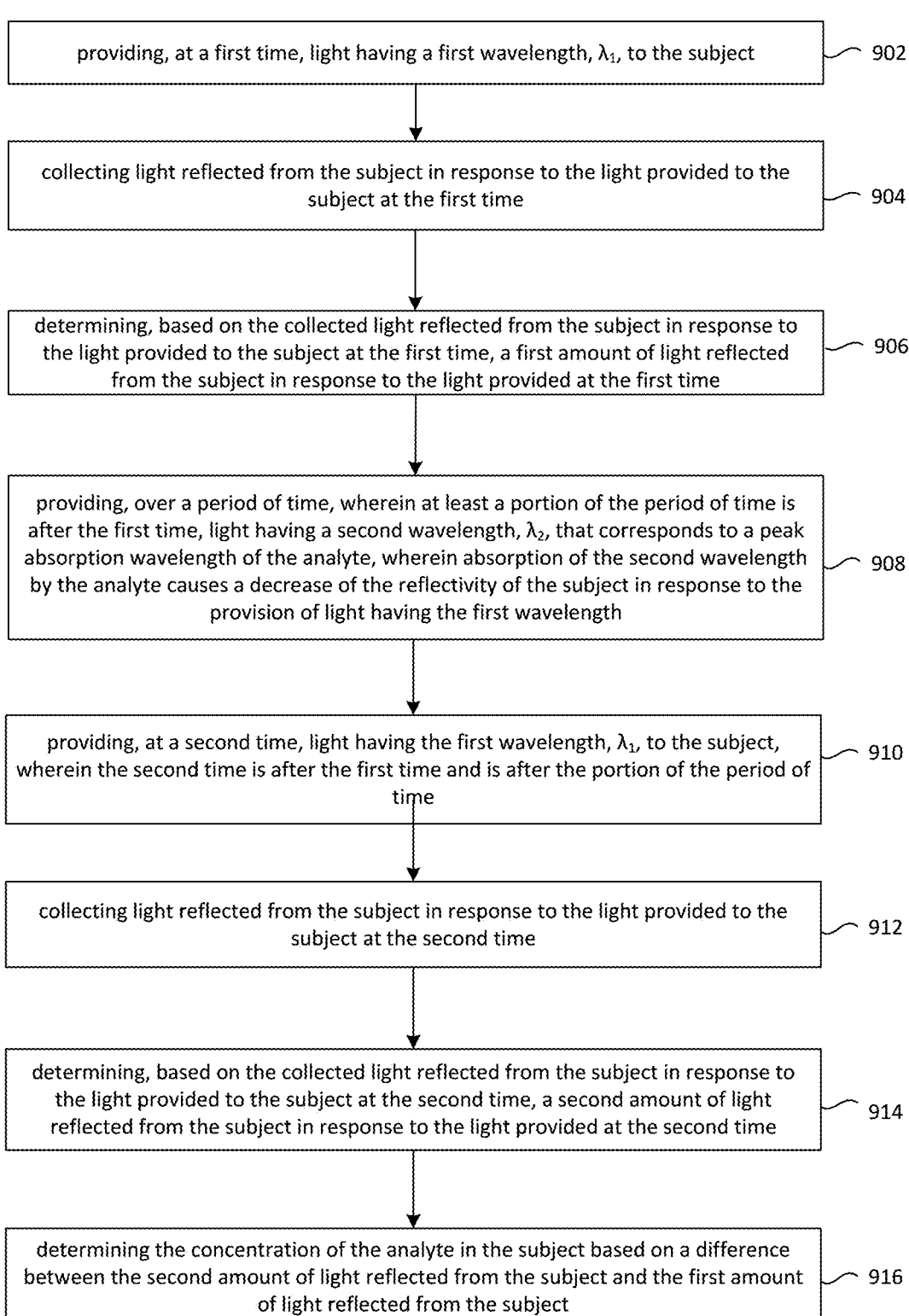

providing, at a first time, light having a first wavelength, $\lambda_1$, to the subject —— 902 collecting light reflected from the subject in response to the light provided to the subject at the first time —— 904 determining, based on the collected light reflected from the subject in response to the light provided to the subject at the first time, a first amount of light reflected from the subject in response to the light provided at the first time —— 906 providing, over a period of time, wherein at least a portion of the period of time is after the first time, light having a second wavelength, $\lambda_2$, that corresponds to a peak absorption wavelength of the analyte, wherein absorption of the second wavelength by the analyte causes a decrease of the reflectivity of the subject in response to the provision of light having the first wavelength —— 908 providing, at a second time, light having the first wavelength, $\lambda_1$, to the subject, wherein the second time is after the first time and is after the portion of the period of time —— 910 collecting light reflected from the subject in response to the light provided to the subject at the second time —— 912 determining, based on the collected light reflected from the subject in response to the light provided to the subject at the second time, a second amount of light reflected from the subject in response to the light provided at the second time —— 914 determining the concentration of the analyte in the subject based on a difference between the second amount of light reflected from the subject and the first amount of light reflected from the subject —— 916

FIG. 9

NON-INVASIVE BILIRUBIN DETECTION USING INDUCED PHOTOREACTION

CROSS-REFERENCE TO RELATED APPLICATION

This application claims the benefit of and priority to U.S. Provisional Application No. 63/380,888, filed Oct. 22, 2022, which is incorporated by reference herein in its entirety.

TECHNICAL FIELD

This disclosure relates generally to the non-invasive detection of a concentration of an analyte in a subject, and more specifically, to non-invasive bilirubin detection through induced photoreaction.

BACKGROUND

Techniques to quantify the bilirubin concentration in a patient, for example, when used during phototherapy treatment of jaundice, often require blood to be drawn from the patient, which can cause pain and trauma to the patient, especially a newborn, and can result in infections. Some non-invasive techniques and devices are available for measuring bilirubin concentrations. However, because existing non-invasive techniques and devices are sensitive to skin pigmentation of the patient and are generally limited to detecting bilirubin concentrations of 20 mg/dl or less, they are primarily used as screening tools.

Therefore, there is a need for reliable, non-invasive sensors for bilirubin detection in newborns.

SUMMARY

In some aspects, the techniques described herein relate to a method of determining a concentration of analyte in a subject. The method includes collecting light reflected from a subject in response to light having a first wavelength, $\lambda_1$, that is provided to the subject at a first time, and determining, based on the collected light, a first reflectivity of the subject in response to the light provided at the first time. The method further includes providing, over a period of time, light having a second wavelength, $\lambda_2$, that corresponds to an absorption wavelength of the analyte, where absorption of the second wavelength by the analyte causes a change of the reflectivity of the subject, and collecting light reflected from the subject in response to light having the first wavelength, $\lambda_1$, that is provided to the subject at a second time, where the second time is after the period of time. Based on the collected light, a second reflectivity of the subject in response to the light provided at the second time is determined. The concentration of the analyte in the subject is determined based on a difference between the second reflectivity and the first reflectivity.

In some aspects, the techniques described herein relate to a system for determining a concentration of analyte in a subject. The system includes: a first light source configured for providing light having a first wavelength, $\lambda_1$, to the subject; a second light source configured for providing light having a second wavelength, $\lambda_2$, that corresponds to an absorption wavelength of the analyte, where absorption of the second wavelength by the analyte causes a decrease of a reflectivity of the subject in response to the providing of light having the first wavelength. The system includes: a detector configured for detecting light reflected from the subject in response to the light provided to the subject; and a computing device configured for: controlling the first light source to provide the light having the first wavelength, $\lambda_1$, to the subject at a first time and at a second time after the first time; controlling the second light source to provide the light having the second wavelength, $\lambda_2$, to the subject over a period of time, where at least a portion of the period of time is after the first time and before the second time; determining, based on the detected light, a first reflectivity of light reflected from the subject in response to the light provided at the first time, determining, based on the detected light, a second reflectivity of light reflected from the subject in response to the light provided at the second time, and determining the concentration of the analyte in the subject based on a difference between the second reflectivity and the first reflectivity.

BRIEF DESCRIPTION OF THE DRAWINGS

FIGS. 8A and 8B is a schematic side and top views of an apparatus 800 for implementing the techniques described herein.

FIG. 9 is a flowchart of a process for determining the concentration of analyte in a subject according to an aspect of the disclosure.

DETAILED DESCRIPTION

Figure 1:
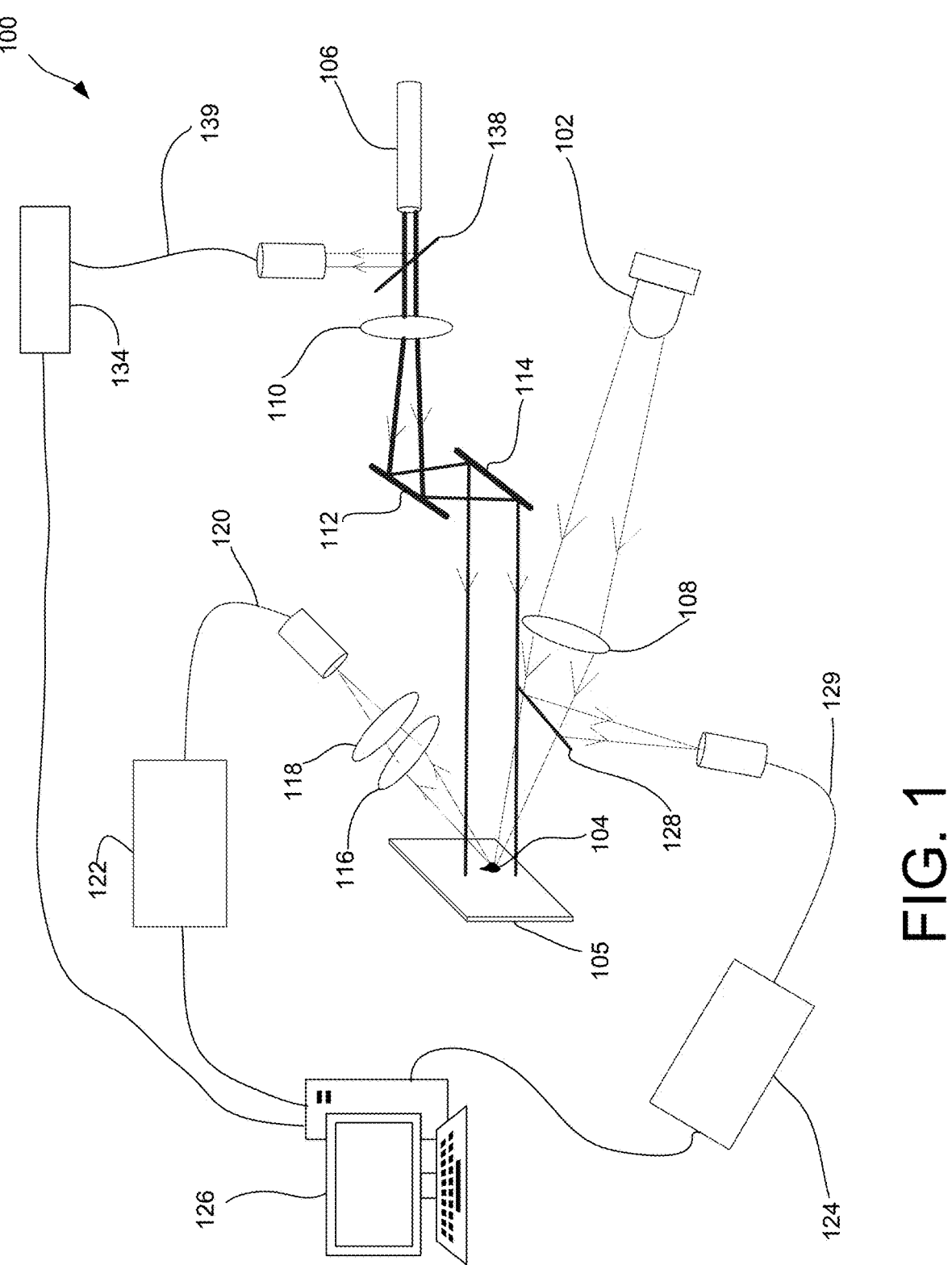
FIG. 1 is a block diagram of a system for determining the concentration of an analyte in a subject according to an aspect.

This disclosure relates to techniques and systems for detecting an analyte in a subject. Light having a particular spectrum is provided to the subject to induce photoreactions in analytes in subject, where photoreactions cause a change in the reflectivity of the subject to light having a second spectrum. The reflectance of the subject can be measured at a plurality of times before, during, and/or after the light of the first spectrum is provided to the subject. Where the rate of change of the reflectivity in response to the provision of the light having the first spectrum is proportional to a concentration of the analyte in the subject, the rate of change of the reflectance can be determined from the plurality of measurements of the reflectance, and then the concentration of the analyte can be determined from the rate of change. Because this technique is differential in nature, in that it relies on measurements of a dimensionless change in the reflectance rather than on measurements of the value of the reflectance, when the subject is a human and the light is provided transcutaneously to the subject, the techniques disclosed herein have the technical advantage of being relatively insensitive to skin pigmentation and other external factors, as compared with existing techniques. In addition, the techniques disclosed herein have the technical advantage of being able to reliably and accurately measure for high analyte concentrations, in contrast to other existing techniques.

In general, the implementations are directed to medical devices and methods. The term patient, subject, sample, or user may hereinafter be used for a person who benefits from the medical devices or the methods disclosed in the present disclosure. For example, the patient can be a person whose body contacted by, engaged with, or otherwise interacts with the medical device.

In some implementations, a system or device is configured to make measurements of an analyte in a patient. In some cases, the system or device is configured to take measurements of an analyte concentration of a patient that have a likelihood of being accurate. For example, in some implementations, the system or device is configured to analyze concentration measurements non-invasively from a patient based on light reflectance measurements taken from the patient before, during, and/or after a photoreaction of the analyte is induced in the patient. Accordingly, in some implementations, the analyte concentration measurements may not require drawing blood from the patient.

In some implementations, the techniques disclosed herein relate to measuring a concentration of bilirubin in a patient. Bilirubin is a natural byproduct or a process in which red blood cells are broken down in the body. The adult liver converts unconjugated bilirubin into a conjugated form, that be excreted from the body. However, hyperbilirubinemia is a common condition in newborns in which excessive amounts of bilirubin buildup in the blood, causing jaundice. At elevated concentrations, bilirubin can be toxic to humans, and therefore therapies exist assist the excretion of bilirubin from a newborn's body.

Four structural isomers of bilirubin are ZZ-bilirubin, ZE-bilirubin, EE-bilirubin, and EZ-bilirubin. ZZ-bilirubin is the stable, more insoluble form and contributes to hyperbilirubinemia, while ZE-bilirubin, EE-bilirubin, and EZ-bilirubin are known as lumirubins, which are significantly more hydrophilic than ZZ-bilirubin and its configurational isomers. Therefore, lumirubins dissolve well in water and blood and are easily excreted into bile or urine, which is then removed from the body. Phototherapy with blue light provided to the skin of a newborn causes isomerization of the ZZ-bilirubin molecules found in the skin and with formation of low-toxicity lumirubin, which then is absorbed into the blood and removed from the body. ZZ-bilirubin molecules from the blood replace the isomerized bilirubin in the subcutaneous tissue and also undergo isomerization and then are removed from the body. Phototherapy can be applied in a number of treatment cycles to reduce the serum bilirubin concentrations in the body of a patient.

With the assumption that the bilirubin concentrations in the skin tissue and blood of a newborn are in equilibrium before beginning a phototherapy treatment cycle, measurement of subcutaneous bilirubin concentrations can be used to measure serum concentrations of bilirubin in a patient.

FIG. 1 is a block diagram of a system 100 for determining the concentration of an analyte in a subject according to an aspect. The system 100 includes a first light source 102 that is configured for providing light having a first wavelength to a sample 104. The sample 104 can be mounted on a stage 105. In some implementations, the first light source 102 can include a narrowband light source (e.g., a laser or a LED) that emits a light spectrum with a FWHM of less than 5 nm. In some implementations, the first light source 102 can include a broadband light source (e.g., a halogen lamp, a blue or white light LED, etc.) that emits a continuous light spectrum with a FWHM greater than 10 nm. When the analyte is bilirubin, the first light source 102 can emit a continuous spectrum of light, for example, white light, or at least including wavelengths in the range of 480 nm to 520 nm. Light from the first light source 102 can be focused on the sample 104 by a lens 108.

The system 100 includes a second light source 106 that is configured for providing light having a second wavelength to the sample 104. In some implementations, the second wavelength can correspond to an absorption wavelength of the analyte whose concentration in a sample 104 is determined by the system 100. For example, the second wavelength can be within 25 nm of the peak absorption wavelength of the analyte, where the peak absorption wavelength is a wavelength at which an absorption cross section of the analyte is maximized. In some implementations, the light provided by the second light source can include one or more second wavelengths within an absorption band of the analyte (e.g., can cover the entire absorption band of the analyte). In some implementations, absorption of the second wavelength of light provided by the second light source 106 by the analyte can cause a decrease in the reflectivity of the sample 104 in response to light provided by the first light source 102 to the sample 104. When the analyte is bilirubin, the second wavelength can include a wavelength in the range of 425 nm to 475 nm. Light from the second light source 106 can be focused on the sample 104 by a lens 110 and can be positioned at a location of the sample 104 by scanning mirrors 112, 114, where the location can coincide with a location of the focus of the light provided by the first light source 102 to the sample 104. In some implementations the spot size (e.g., an area or a diameter) of the focused light from the first light source 102 can be greater than or equal to the spot size (e.g., a respective area or diameter) of the focused light from the second light source 106.

The system 100 can include a detector, or a detector assembly, where the detector includes a focusing lens 116, a band pass filter 118, an optical fiber 120, and a reflected light spectrometer 122. The optical fiber 120 routes light reflected from the sample 104 in response to the provision of light from the first light source 102 to the sample 104 to the reflected light spectrometer 122. The band pass filter 118 ensures that a range of wavelengths of the reflected light reaches the spectrometer 122, while wavelengths outside the range are blocked from reaching the spectrometer 122. For example, when the analyte is bilirubin, the wavelength range of the bandpass filter can be about 480 nm to about 520 nm. The band pass filter 118 can be located between the sample 104 and the entrance to the optical fiber 120, within the optical fiber 120, or between the optical fiber 120 and the spectrometer 122.

The system 100 also includes a first calibration spectrometer 124. A portion of the light provided to the sample 104 from the first light source 102 can be picked off by a beam splitter 128 and directed (e.g., through an optical fiber 129) to the first calibration spectrometer 124. Thus, the first calibration spectrometer 124 can measure a spectrum of light provided to the sample 104 by the first light source 102, and the reflected light spectrometer 122 can measure a spectrum of light reflected from the sample 104 in response to the light provided to the sample 104 by the first light source 102. The system 100 also can include a second calibration spectrometer 134. A portion of the light provided to the sample 104 from the second light source 106 can be picked off by a beam splitter 138 and directed (e.g., through an optical fiber 139) to the second calibration spectrometer 134, so that the second calibration spectrometer 134 can measure a spectrum and/or total power of light provided to the sample 104 by the second light source 106. The spectrum and/or total power of the light provided by the second light source can be monitored and controlled by a computing device. In addition, the computing device 126 can compute a reflectivity of the sample 104 based on the spectra measured by the spectrometers 122, 124. The computing device 126 also can control operation of other elements of the system 100, including when, for how long, and at what powers/intensities light from the first and second light sources 102, 106 is provided to the sample 104.

In some implementations, light from the second light source 106 can be provided over a period of time (e.g., 5 seconds, 10 seconds, 20 seconds, 40 seconds, 120 seconds, 180 seconds) to the sample 104 to induce photoreactions of the analytes in the sample 104, where the photoreactions can reduce the reflectivity of the sample 104 to light provided by the first light source 102. The light reflected from the sample 104 in response to light provided by the first light source 102 can be measured at a first time before, or during, the period of time and at a second time after, or during, the period of time to observe the reduction in the reflectivity of the sample caused by the photoreactions due to light from the second light source 106.

The measurements of the reflected light from the sample 104 can be used to determine a rate of change of the reflectivity of the sample due to the induced photoreactions in the sample. In some implementations, the rate of change of the reflectivity can be proportional to a concentration of the analyte in the sample 104, and the concentration of the analyte can be determined from the determined rate of change of the reflectivity. For example, when the intensity of the light from the second light source 106 is well below a saturation intensity of the photoreaction that is induced by the light, the number of molecules converted to a lower reflecting state by the light from the second light source per unit time is proportional to the concentration of the molecules. Therefore, the rate of change of the reflectivity can be proportional to the concentration of analyte molecules in the sample.

In some implementations, light reflected from the sample 104 in response to light provided by the first light source 102 can be measured at a plurality of times during the period of time to observe the reduction of the reflectivity of the sample 104 at multiple times and/or to gather more data to determine a rate of change of the reduction of the reflectivity of the sample due to the photoreactions within the sample 104. For example, multiple data points of the reflectivity measured at different times, when the reflectivity of the sample decreases due to the induced photoreactions can be used to fit a slope to a reflection vs. time graph to determine the rate of decrease of the reflectivity.

Figure 2A:
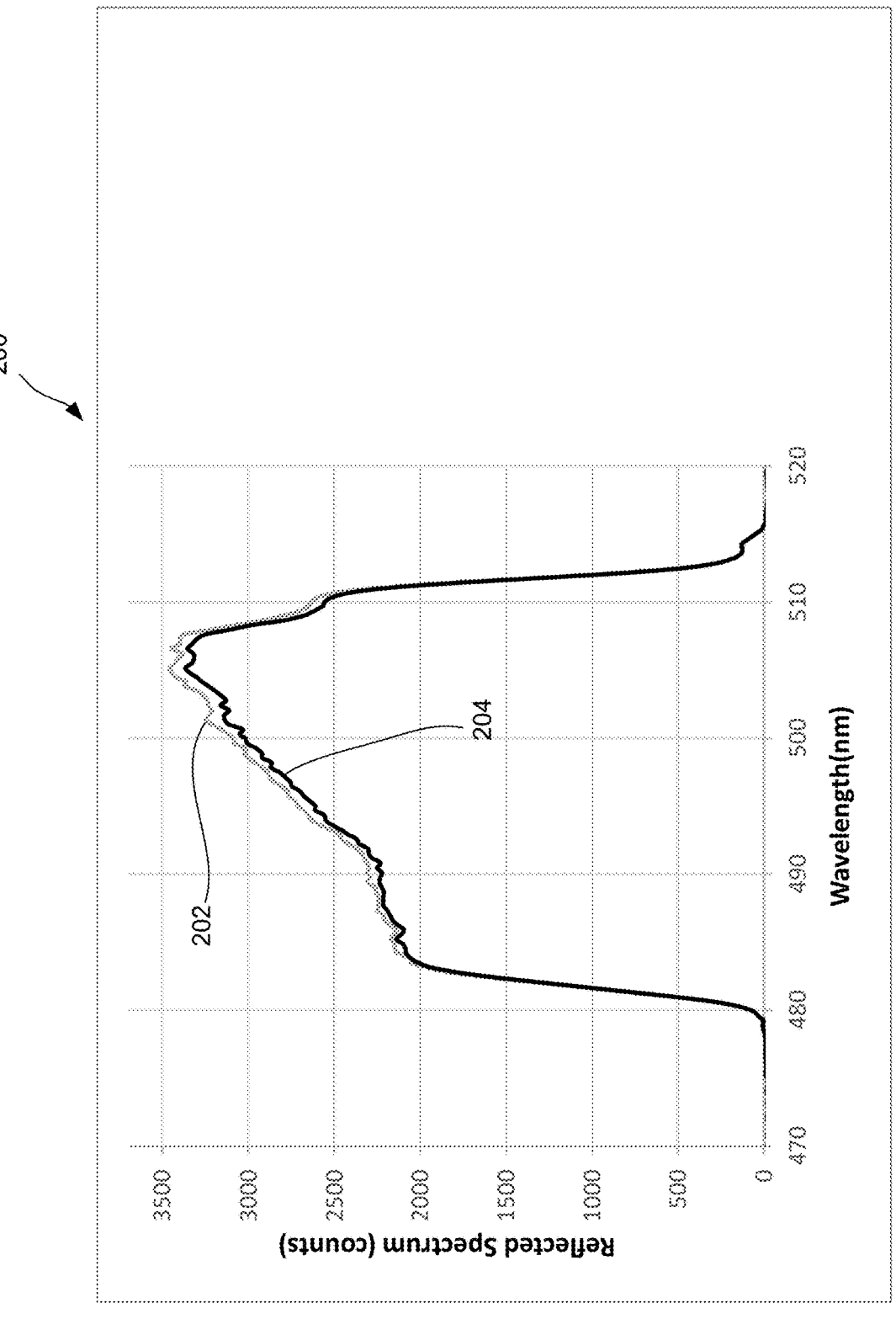
FIG. 2A is an example graph showing the effect of induced photoreactions on analyte molecules in a subject on the reflected spectrum of the subject.

FIG. 2A is an example graph 200 showing the effect of induced photoreactions on analyte molecules in a sample on the reflected spectrum of the sample. The graph 200 includes a first reflected light spectrum 202 for a sample that includes bilirubin over a wavelength range of about 480 nm to about 520 nm in response to white light being provided to the sample. The graph 200 shows a plot of reflected light intensity (in arbitrary units) versus wavelength. After light having a wavelength that induces photoreactions in the bilirubin at the sample is provided to the sample, a second reflected light spectrum 204 (collected in response to a same intensity of white light that produced the first reflected light spectrum 202) indicates a reduced reflectivity of the sample due to the induced photoreactions.

Figure 2B:
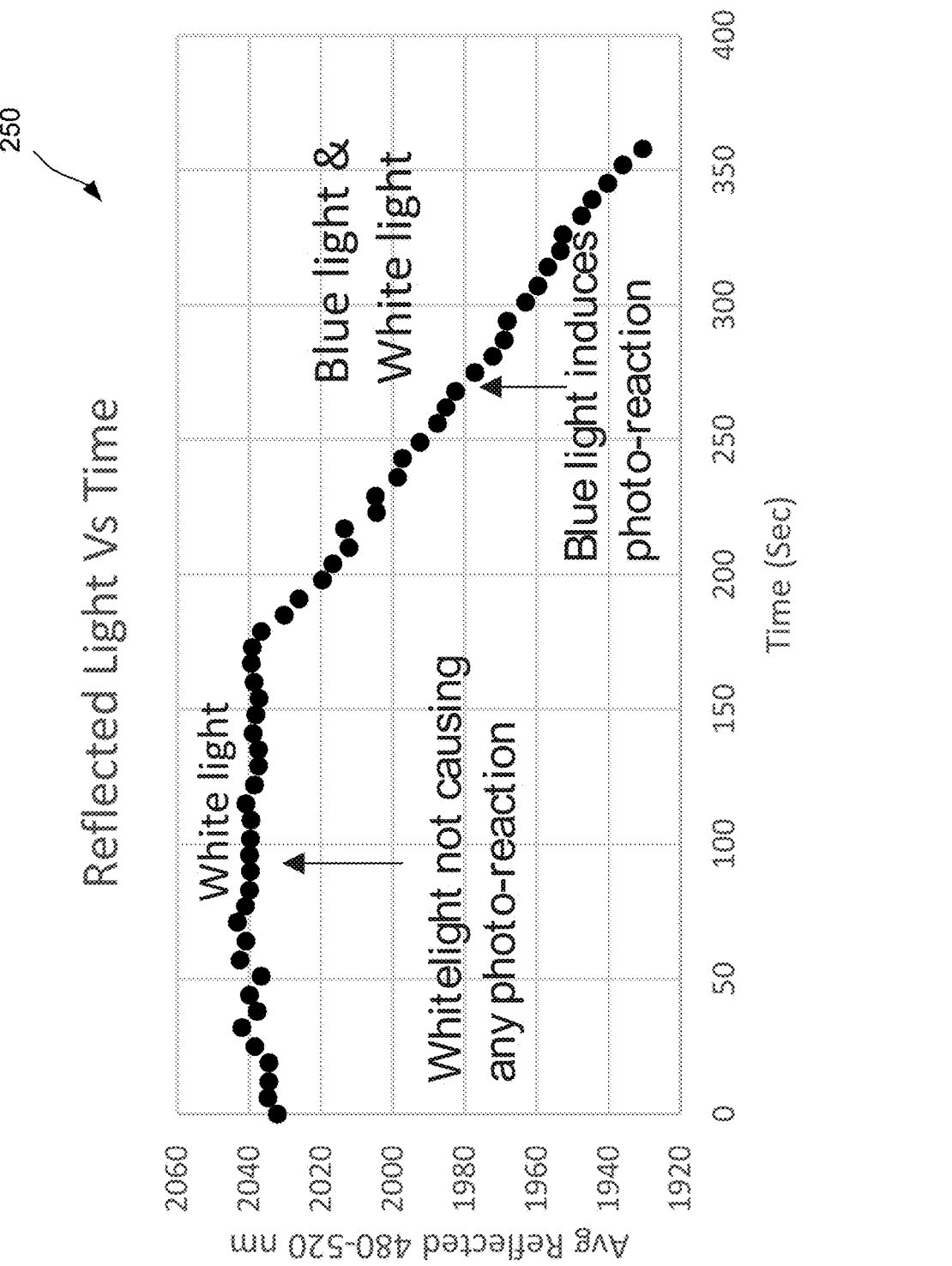
FIG. 2B is an example graph showing the effect of induced photoreactions of bilirubin molecules in a subject on the reflectance of the subject as photoreactions occur in the subject.

FIG. 2B is an example graph 250 showing the effect of induced photoreactions of bilirubin molecules in a sample on the reflectance of the sample as photoreactions occur in the sample. Each data point in the graph 250 represents an average reflectance of the sample over a wavelength range of 480 nm to 520 nm at a particular sequential time in an experiment. In the experiment, the reflectance of the sample in response to white light is measured and recorded for times t=0 seconds to t=180 seconds. From times t=180 seconds to t=356 seconds, blue light having a wavelength that induces photoreactions of the bilirubin molecules is provide to the sample, and the reflectance of the sample in response to white light is measured and recorded. The decrease of the reflectance of the sample in response to the blue light provided to the sample is evident by the negative slope of the plotted points as a function of time.

Figure 3:
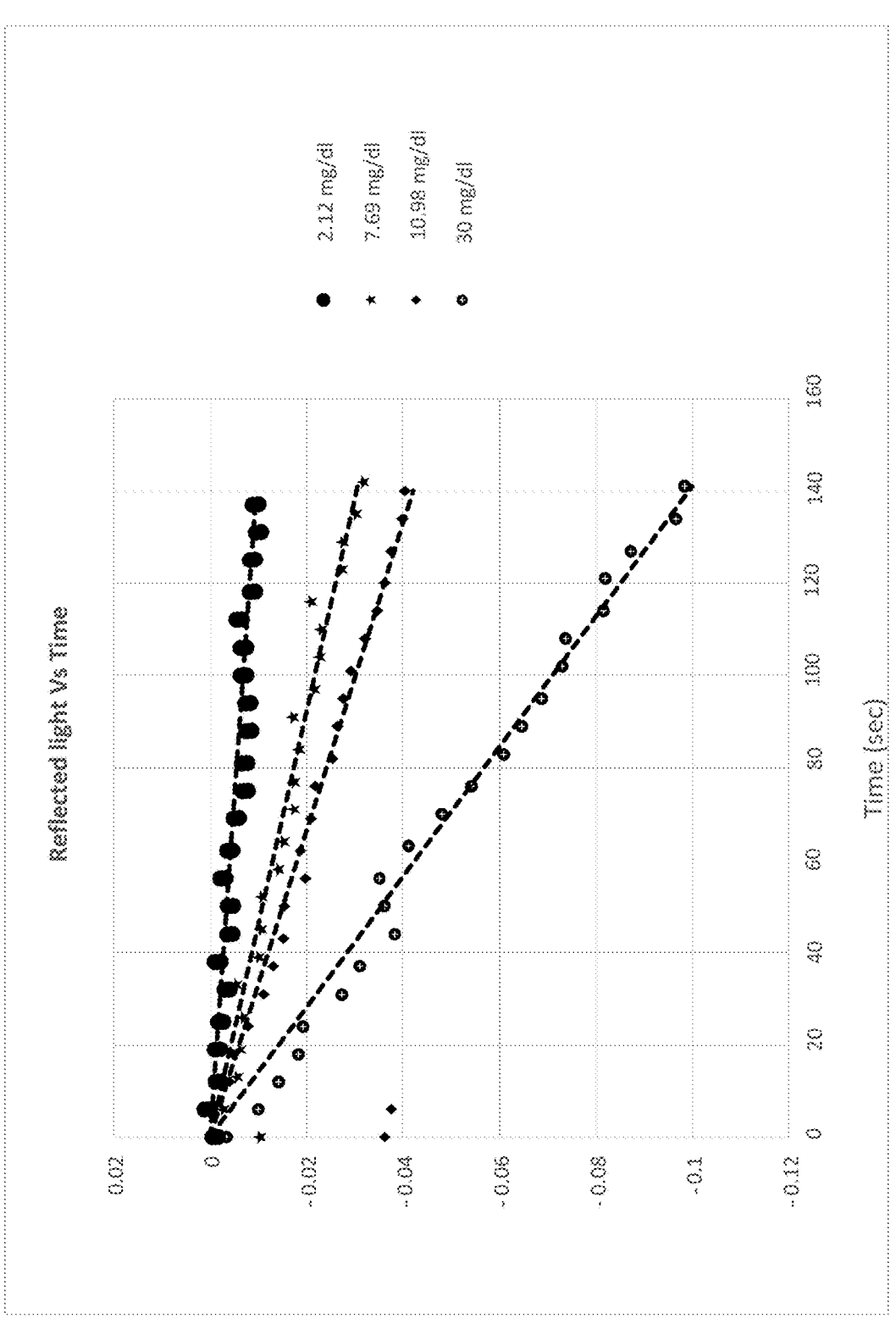
FIG. 3 is an example graph showing, for subjects containing different concentrations of bilirubin, the effect of induced photoreactions of bilirubin molecules in the subjects on the reflectance of white light by the subjects as photoreactions occur over a period of time.

The inventors performed many experiments similar to the one whose results are plotted in the graph 250 of FIG. 2B, where different samples with different known concentrations of bilirubin were used in the different experiments. FIG. 3 is an example graph 300 showing, for samples containing different concentrations of bilirubin, the effect of induced photoreactions of bilirubin molecules in the samples on the reflectance of white light by the samples as photoreactions occur over a second period of time. The graph 300 illustrates the percentage decrease of the reflectance of the sample, measured in dimensionless units on the y-axis, versus the duration of time over which photoreactions are induced in the sample by blue light, measured on the x-axis in seconds. Data for a sample having a concentration of 2 mg/dl are shown by circle data points. Data for a sample having a concentration of 8 mg/dl are shown by star data points. Data for a sample having a concentration of 11 mg/dl are shown by diamond data points. Data for a sample having a concentration of 30 mg/dl are shown by circle with plus sign data points.

For each experiment, a least squares fit of the data was used to determine a slope of the reflectance over time, as shown in FIG. 3, and therefore of a rate of change of the decrease of the reflectance. The inventors discovered that this rate of change remained constant for samples having the same concentrations of bilirubin when the same light intensity of blue light was used to induce photoreactions in the sample. In addition, the inventors discovered that the rate of change for a sample having a particular bilirubin concentration is proportional to the bilirubin concentration.

Figure 4:
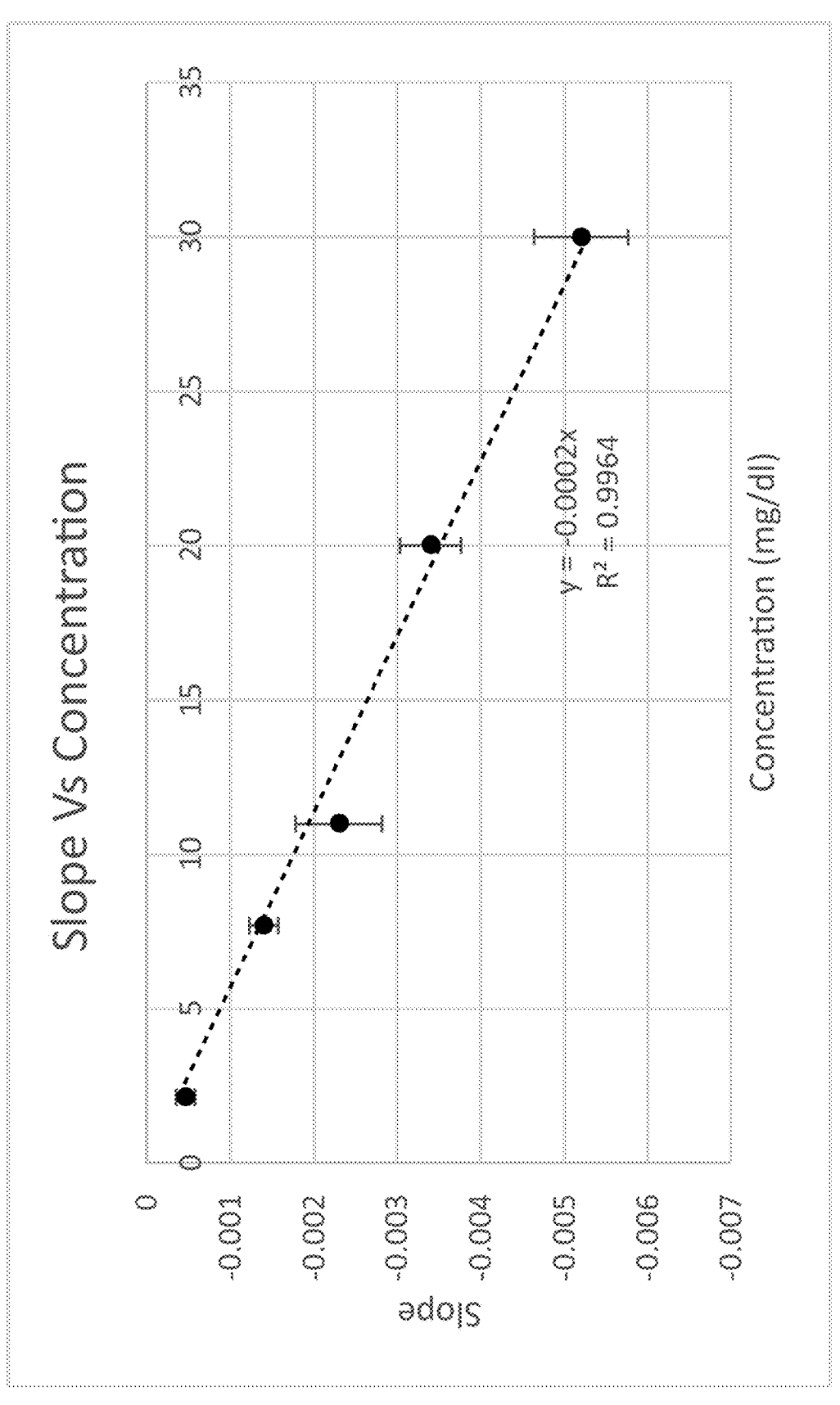
FIG. 4 is an example graph showing, for subjects having different concentrations of bilirubin, a relationship between the slopes of the reflectance of a subject as a function of time when the subject was illuminated by photoreaction-inducing blue light and the concentration of bilirubin in the subject.

FIG. 4 is an example graph 400 showing, for samples having different concentrations of bilirubin, a relationship between the slopes of the reflectance of a sample as a function of time when the sample was illuminated by photoreaction-inducing blue light and the concentration of bilirubin in the sample. The error bars on the data points in the graph 400 show standard deviations of the measured slopes when more than one slope was measured. As can be seen from the fit of the data in the graph 400, the absolute value of the slope is proportional to the concentration of bilirubin in the sample, indicating that the slope (i.e., the rate of change of the reflectance in response to the photoreaction-inducing blue light) is a reliable indicator of the bilirubin concentration in a sample. Because the rate of change of the reflectance is a differential quantity, it is insensitive to errors and variations due to different pigment amounts, different skin thicknesses, etc. of different samples. In addition, as can be seen from the graph 400, the rate of change can be reliably measured for values correlated with bilirubin concentrations of 30 mg/dl, thus providing a technique for measuring higher bilirubin concentrations than other existing techniques.

Figure 5:
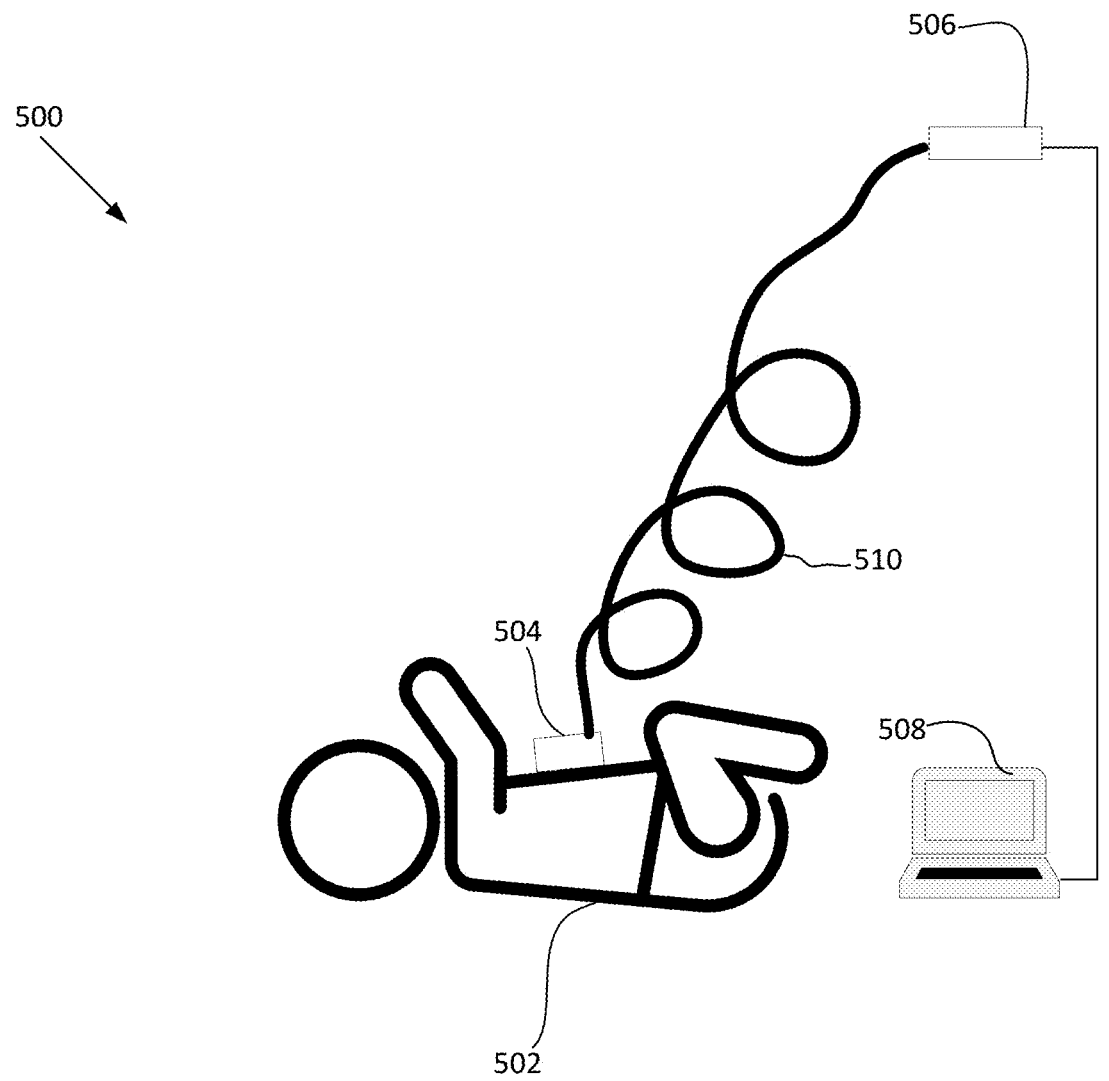
FIG. 5 is an example schematic diagram of a system for measuring a concentration of an analyte in a subject based on reflectance spectra measurements of the subject.

FIG. 5 is an example schematic diagram of a system 500 for measuring a concentration of an analyte in a subject 502 based on reflectance spectra measurements of the subject. For example, the system can be used to measure a concentration of bilirubin in a newborn baby. The system 500 can include a module 504 that can include various components for performing the reflectance spectra measurements on the subject 502. For example, the module 504 can include a housing that is placed in contact with a surface of the subject 502 and can be secure in place on the subject for the duration of the measurements. In some implementations, the module 504 can include a first light source that provides a continuous spectrum of light to the subject 502. For example, the first light source can include a halogen or an LED light source that emits a continuous spectrum of light over a range of wavelengths. The light from the first light source can be provided to the subject 502, for example, in the form of a focused spot. In some implementations, the focused spot can have a FWHM diameter of less than 5 mm. In some implementations, the light from the first light source can be provided to the subject 502 through an optical fiber.

Light reflected by the subject 502 in response to the light from the first light source that is provided to the subject can be collected, and the collected light can be provided to a detector assembly that includes a spectrometer 506 that measures the spectrum of the collected reflected light. In some implementations, the collected light can be provided to the spectrometer 506 by way of an optical fiber 510. The measured reflected spectrum is based on measurements of an amount of reflected light received (e.g., an amplitude, an intensity, or a power of light received) by the spectrometer at different wavelengths within the range of wavelengths over which the spectrometer operates.

The module 504 of the system 500 can include a second light source that provides to the subject 502 light having a wavelength that induces photoreactions in the analyte in the subject 502, where the photoreactions can cause a decrease in the reflectivity of the subject in response to light provided by the first light source. The rate of the photoreactions in the subject, and the rate of change of the reflectivity of the subject, can be proportional to the concentration of the analyte in the subject 502.

In some implementations, light from the second light source can be provided continuously over a period of time (e.g., 5 seconds, 10 seconds, 20 seconds, 40 seconds, 120 seconds, 180 seconds) to the subject 502 to induce photoreactions of the analytes in the subject 502, where the photoreactions can reduce the reflectivity of the subject 502 to light provided by the first light source. Light reflected from the subject 502 in response to light provided by the first light source can be measured at a first time before, or during, the period of time and at a second time after, or during, the period of time to observe the reduction in the reflectivity of the subject caused by the photoreactions due to light from the second light source. In some implementations, light from the first light source can be provided continuously over a period of time (e.g., 5 seconds, 10 seconds, 20 seconds, 40 seconds, 120 seconds, 180 seconds) to the subject 502 to measure a reflectivity of the analytes in the subject 502, while the reflectivity of the subject 502 is reduced in response to light provided by the second light source. Thus, in some implementations, light from both the first and second light sources is provided continuously and simultaneously over a period of time (e.g., 5 seconds, 10 seconds, 20 seconds, 40 seconds, 120 seconds, 180 seconds) to the subject.

The system 500 can include a computing device 508 that includes one or more processors and a memory storing instructions that are executable by the one or more processors to perform the techniques described herein. For example, the memory of the computing device 508 can include one or more look-up tables that correlate a rate of change of the reflectivity of the subject with an analyte concentration of the subject. Spectra measured by the spectrometer 506 can be provided to the computer device 508 that processes, for example, the reflected spectrum data and data about the light provided by the first and second light sources to the subject (e.g., the spectrum of light provided by the first light source to the subject, the intensity of and time at which light is provided by the second light source, the times at which reflected spectra are measured, etc.) to determine a rate of change of the reflectivity of the subject due to the induced photoreactions in the subject.

The computing device 508 can determine a concentration of the analyte in the subject 502 from the determined rate of change of the reflectivity based on the previously established correlation between the rate of change of the reflectivity of the subject with an analyte concentration of the subject. An indication of the analyte concentration in the subject 502 determined by the computing device 508 can be output to a user of the system. For example, a display of the computing device 508 or of the module 504 can output a numerical value indicating the analyte concentration can output other indicia (e.g., colored light, sound, etc.) indicating analyte concentration above or below one or more threshold values.

In different possible implementations, one or more of the first light source, components of the detector assembly (e.g., the spectrometer 506), and the computing device 508 can be included in the module 504 that is coupled to the subject 502 to measure the analyte concentration of the subject. However, in other different possible implementations, one or more of the first light source, the spectrometer 506, and the computing device 508 can be located outside the module 504 that is coupled to the subject 502. Additionally, light from the first light source can be directed to the spectrometer 506, or to another spectrometer, without first being reflected by the subject 502 to calibrate the spectrum of the input light from the first light source.

Figure 6B:
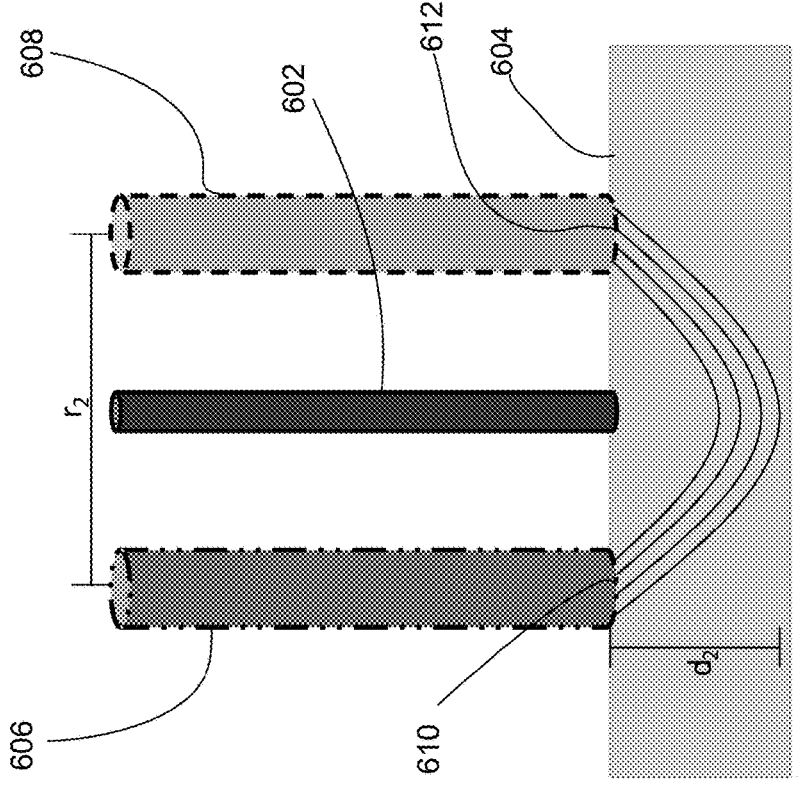
FIG. 6B is a schematic diagram of a second arrangement of the system shown in FIG. 6A, but where the ends of the fibers, respectively, are located at a distance apart from each other in a direction parallel to a surface of the subject.
Figure 6A:
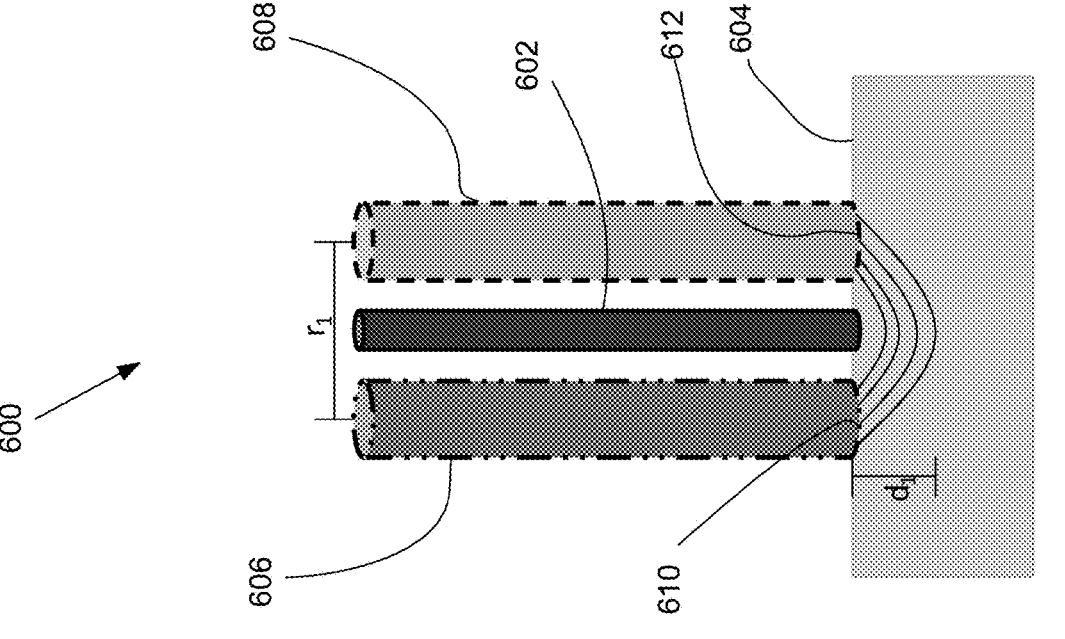
FIG. 6A is a schematic diagram of a first arrangement of a system for measuring a concentration of an analyte in a subject based on reflectance spectra measurements of the subject.

FIG. 6A is a schematic diagram of a first arrangement of a system 600 for measuring a concentration of an analyte in a subject 604 based on reflectance spectra measurements of the subject. The system 600 includes a photoreaction optical fiber 602 that is configured to deliver electromagnetic radiation (e.g., blue light) to a subject 604 to induce photoreactions in analytes in the subject 604. The system 600 also includes a light source optical fiber 606 and a signal collection optical fiber 608 that together can be used to measure a reflectance of the subject 604 as (and/or before or after) electromagnetic radiation is delivered to the subject by the photoreaction optical fiber 602. For example, the light source optical fiber 606 can deliver a broad spectrum of light (e.g., at least over 480 nm to 520 nm when measuring bilirubin concentrations in the subject) to the subject 604, where the broad spectrum of light is emitted from the fiber 606 and delivered to the subject 604 from a first end 610 of the fiber, were the first end 610 is proximate to the subject 604. The broad spectrum of light from the fiber 606 is reflected from the subject 604, and the reflected light is collected by the signal collection optical fiber 608 through a second end 612 of the fiber 608, where the second end 612 is proximate to the subject 604. In some implementations, light from the light source optical fiber 606 can be provided in a direction normal to a surface of the subject, but an emission angle of light from the fiber can cause light to penetrate into the subject and to be reflected from within the subject at an angle that directs the reflected light toward an entrance to the signal collection optical fiber 608. In some implementations, light from the light source optical fiber 606 can be provided to a surface of the subject at a non-zero angle to the normal direction, such that light is reflected from within the subject at an angle that directs the reflected light toward an entrance to the signal collection optical fiber 608.

The first end 610 and the second end 612 can be located a distance $r_1$ apart from each other in a direction parallel to a surface of the subject 604. Based on the distance $r_1$, the reflected light that is collected by the signal collection optical fiber 608 is reflected from portions of the subject located at an average depth $d_1$ below the surface of the subject, where the average depth is proportional to the distance $r_1$ between the ends 610, 612.

FIG. 6B is a schematic diagram of a second arrangement of the system 600 shown in FIG. 6A, but where the ends 610, 612 of the fibers 606, 608, respectively, are located at a distance $r_2$ apart from each other in a direction parallel to a surface of the subject 604. Based on the distance $r_2$, the reflected light that is collected by the signal collection optical fiber 608 is reflected from portions of the subject located at an average depth $d_2$ below the surface of the subject. When the distance $r_2$ is greater than $r_1$, then the depth $d_2$ is greater than the depth $d_1$.

Figures 7A, 7B:
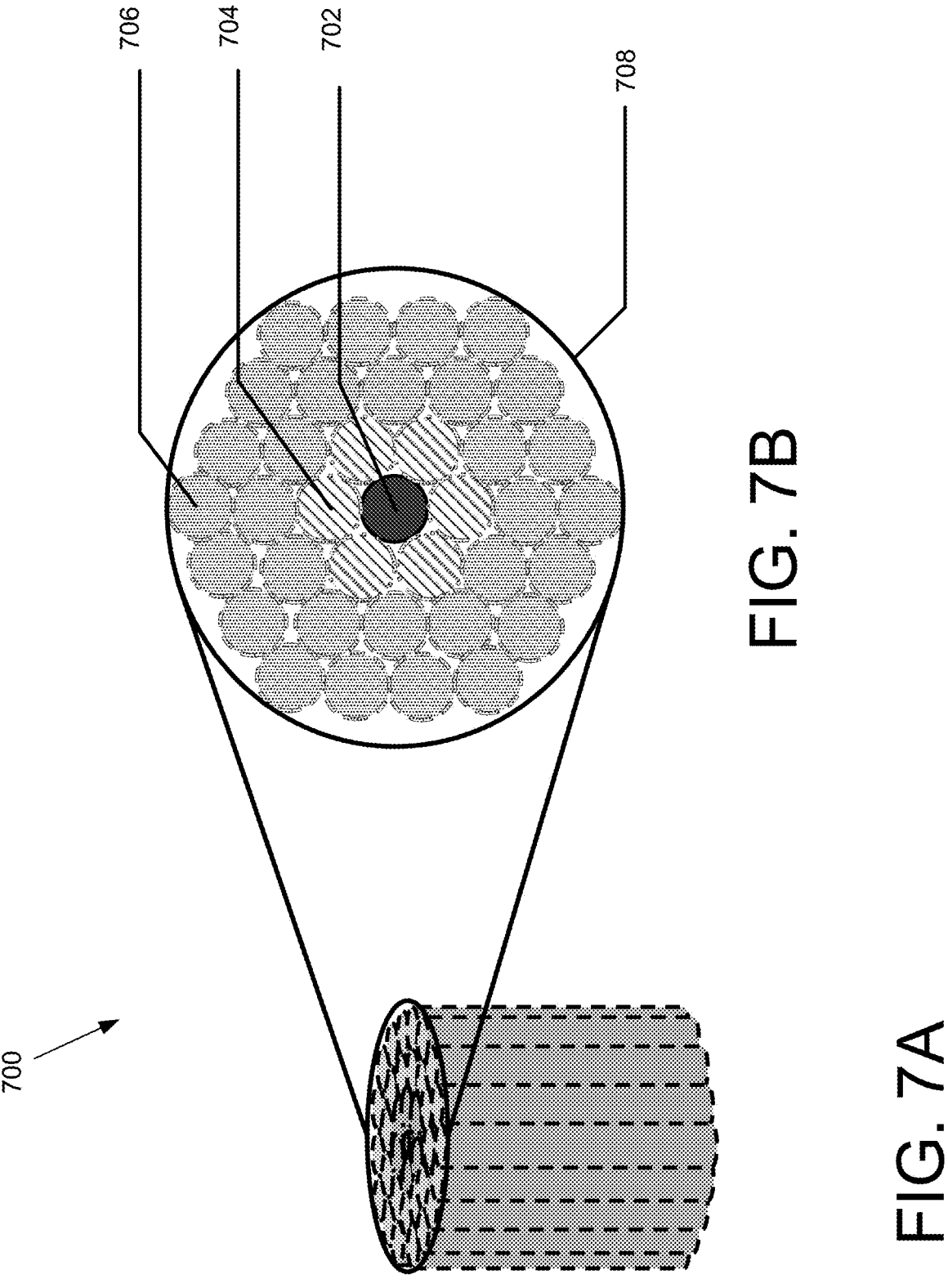
FIG. 7A is a schematic perspective view of a bundle of a plurality of optical fibers.
FIG. 7B is a schematic end view of the bundle of optical fibers of FIG. 7A.

FIG. 7A is a schematic perspective view of a bundle 700 of a plurality of optical fibers, and FIG. 7B is a schematic end view of the bundle 700 of optical fibers of FIG. 7A. The bundle 700 includes a photoreaction optical fiber 702, one or more light source optical fibers 704, and one or more signal collection optical fibers 706. In some implementations, the bundle 700 includes only one light source optical fiber 704 and a plurality of signal collection optical fibers 706. In some implementations, the bundle 700 includes a plurality of light source optical fibers 704 and only one signal collection optical fiber 706. In some implementations, the bundle 700 includes a plurality of light source optical fibers 704 and a plurality of signal collection optical fiber 706. The bundle 700 of optical fibers 702, 704, 706 can be contained within a jacket 708 that encloses a common bundle 700 of the optical fibers.

The photoreaction optical fiber(s) 702 is/are configured to deliver electromagnetic radiation to induce photoreactions of analytes in a subject. The light source optical fiber(s) 704 and the signal collection optical fiber(s) 706 can be used together to monitor a decrease of reflectivity of the subject as the electromagnetic radiation to induce photoreactions of analytes is delivered to the subject by the photoreaction optical fiber 702. For example, broad spectrum of light can be delivered to the subject though a light source optical fiber 704, and the broad spectrum of light from the fiber 704 is reflected from the subject, and the reflected light is collected by a signal collection optical fiber 706. The source optical fiber 704 through which the broad spectrum light is delivered and the signal collection optical fiber 706 that collects the reflected light can be selected based on the lateral distance in a direction parallel to a surface of the subject between a first end of the source optical fiber 704 through which the broad spectrum light is delivered and a second end of the signal collection optical fiber 706 that collects the reflected light, where the fibers are selected to determine an average depth within the subject from which the reflected light is collected. The reflected spectra collected from one or more signal collection optical fibers located at different distanced from light source optical fiber(s) 704 can be processed to determine analyte concentrations in the subject at different depths in the subject.

FIGS. 8A and 8B is a schematic side and top views of an apparatus 800 for implementing the techniques described herein. The apparatus can include a housing 802 that can fit onto a body part of a human subject. For example, in one implementation the housing 802 can form a cavity that is open at at least one end of the housing, where the cavity is sized to receive an appendage (e.g., a finger) 804 of the human subject.

The housing 802 can include one or more first light sources 806, one or more second light sources 808, and one or more photodetectors 810. The one or more first light sources 804 can be configured to emit light having a first spectrum corresponding to an absorption band of an analyte in the subject, where absorption of light from the first light source(s) 804 causes a change in the reflectivity of the subject. The one or more second light sources 806 can be configured to emit light having a second spectrum (e.g., white light) that can be provided to the subject, reflected from the subject, and whose reflected light can be detected by the one or more photodetectors 810. Light from the one or more second light sources 806 can be provided to the subject over a period of time (e.g., continuously over the period of time or at different discrete times during the period of time), while the reflectivity of the subject changes due to the provision of light from the one or more first light sources. The change of the reflectivity of the subject over the period of time (e.g., the rate of change of the reflectivity) due to the provision of light from one or more first light sources 804 can be used to determine a concentration of the analyte according to the techniques described herein.

FIG. 9 is a flowchart of a process 900 for determining the concentration of analyte in a subject according to an aspect of the disclosure. The process 900 includes providing, at a first time, light having a first wavelength, $\lambda_1$, to the subject (902). The process 900 further includes collecting light reflected from the subject in response to the light provided to the subject at the first time (904). The process 900 further includes determining, based on the collected light reflected from the subject in response to the light provided to the subject at the first time, a first amount of light reflected from the subject in response to the light provided at the first time (906). The process 900 further includes providing, over a period of time, where at least a portion of the period of time is after the first time, light having a second wavelength, $\lambda_2$, that corresponds to an absorption wavelength of the analyte, where absorption of the second wavelength by the analyte causes a decrease of the reflectivity of the subject in response to the provision of light having the first wavelength (908).

The process 900 further includes providing, at a second time, light having the first wavelength, $\lambda_1$, to the subject, where the second time is after the first time and is after the portion of the period of time (910). The process 900 further includes collecting light reflected from the subject in response to the light provided to the subject at the second time (912). The process 900 further includes determining, based on the collected light reflected from the subject in response to the light provided to the subject at the second time, a second amount of light reflected from the subject in response to the light provided at the second time (914). The process 900 further includes determining the concentration of the analyte in the subject based on a difference between the second amount of light reflected from the subject and the first amount of light reflected from the subject (916).

In the following, some examples are provided.

Example 1: A method of determining a concentration of analyte in a subject, the method including: collecting light reflected from a subject in response to light having a first wavelength, $\lambda_1$, that is provided to the subject at a first time; determining, based on the collected light, a first reflectivity of the subject in response to the light provided at the first time; providing, over a period of time, light having a second wavelength, $\lambda_2$, that corresponds to an absorption wavelength of the analyte, wherein absorption of the second wavelength by the analyte causes a change of the reflectivity of the subject; collecting light reflected from the subject in response to light having the first wavelength, $\lambda_1$, that is provided to the subject at a second time, wherein the second time is after the period of time; determining, based on the collected light, a second reflectivity of the subject in response to the light provided at the second time; determining the concentration of the analyte in the subject based on a difference between the second reflectivity and the first reflectivity.

Example 2: The method of example 1, where absorption of the light having the second wavelength by the analyte causes isomerization of the analyte in the subject.

Example 3: The method of example 1 or of example 2, where absorption of the light having the second wavelength by the analyte increases a solubility of the analyte in water.

Example 4: The method of any of the preceding examples, further comprising: determining a rate of change of a reflectivity of the subject during the period of time based on a difference between the second amount of light reflected from the subject and the first amount of light reflected the subject; and determining the concentration based on the rate of change of the reflectivity of the subject.

Example 5: The method of any of the preceding examples, where providing the light having the first wavelength includes providing the light having the first wavelength transcutaneously to the subject and where providing the light having the second wavelength includes providing the light having the second wavelength transcutaneously to the subject.

Example 6: The method of any of the preceding examples, where the second wavelength, $\lambda_2$, is a wavelength in a range of 425 nm to 475 nm, and where the analyte is bilirubin.

Example 7: The method of any of the preceding examples, where the first wavelength, $\lambda_1$, is a wavelength in a range of 480 nm to 520 nm, where the second wavelength, $\lambda_2$, is a wavelength in a range of 425 nm to 475 nm, and where the analyte is bilirubin.

Example 8: The method of any of the preceding examples, where providing, at the first time, light having the first wavelength, $\lambda_1$, to the subject, includes providing a continuous spectrum of light having a wavelength within a range of 480 nm and 520 nm to the subject at the first time, where providing, at the second time, light having the first wavelength, $\lambda_1$, to the subject, includes providing a continuous spectrum of light having a wavelength within a range of 480 nm and 520 nm to the subject at the second time, where the second wavelength, $\lambda_2$, is a wavelength in a range of 425 nm to 475 nm, and where the analyte is bilirubin.

Example 9: The method of any of the preceding examples, where providing, at a first time, light having the first wavelength, $\lambda_1$, to the subject includes providing the light having the first wavelength to a first location of a surface of the subject, where providing, at a second time, light having the first wavelength, $\lambda_1$, to the subject includes providing the light having the first wavelength to the first location of the light having the first wavelength to the first location of the surface of the subject, where collecting light reflected from the subject in response to the light provided to the subject at the first time and in response to the light provided to the subject at the first time includes collecting, at a plurality of second locations of the surface of the subject, the light reflected from the subject, where each of the second locations is a different distance from the first location, and further comprising: determining concentrations of the analyte at different depths in the subject based on differences between the second amount of light reflected from the subject and the first amount of light reflected from the subject for the different distances between the first location and each of the second distances.

Example 10: The method of any of the preceding examples, where determining the first amount of light reflected from the subject in response to the light provided at the first time includes determining a first reflectivity of the subject at the first time, where determining the second amount of light reflected from the subject in response to the light provided at the second time includes determining a second reflectivity of the subject at the second time, and where determining the concentration of the analyte in the subject includes determining the concentration based on a difference between the first reflectivity and the second reflectivity.

Example 11: The method of any of the preceding examples, where a first spot size on the subject of the light having the first wavelength is greater than or equal to a second spot size on the subject of the light having the second wavelength.

Example 12: The method of any of the preceding examples, where the light having the first wavelength, $\lambda_1$, and the light having the second wavelength, $\lambda_2$, is provided continuously to the subject and simultaneously is provided continuously to the subject for a time period of at least five seconds.

Example 13: A system for determining a concentration of analyte in a subject, the system comprising: a first light source configured for providing light having a first wavelength, $\lambda_1$, to the subject; a second light source configured for providing light having a second wavelength, $\lambda_2$, that corresponds to an absorption wavelength of the analyte, wherein absorption of the second wavelength by the analyte causes a decrease of a reflectivity of the subject in response to the providing of light having the first wavelength; a detector configured for detecting light reflected from the subject in response to the light provided to the subject; a computing device configured for: controlling the first light source to provide the light having the first wavelength, $\lambda_1$, to the subject at a first time and at a second time after the first time controlling the second light source to provide the light having the second wavelength, $\lambda_2$, to the subject over a period of time, wherein at least a portion of the period of time is after the first time and before the second time; determining, based on the detected light, a first reflectivity of light reflected from the subject in response to the light provided at the first time, determining, based on the detected light, a second reflectivity of light reflected from the subject in response to the light provided at the second time, and determining the concentration of the analyte in the subject based on a difference between the second reflectivity and the first reflectivity.

Example 14: The system of example 13, where absorption of the light having the second wavelength by the analyte causes isomerization of the analyte in the subject.

Example 15: The system of example 13 or example 14, where absorption of the light having the second wavelength by the analyte increases a solubility of the analyte in water.

Example 16: The system of any one of examples 13-15, where the computing device is further configured for: determining a rate of change of a reflectivity of the subject during the period of time based on a difference between the second amount of light reflected from the subject and the first amount of light reflected the subject, and determining the concentration based on the rate of change of the reflectivity of the subject.

Example 17: The system of any one of examples 13-16, where providing the light having the first wavelength includes providing the light having the first wavelength transcutaneously to the subject and where providing the light having the second wavelength includes providing the light having the second wavelength transcutaneously to the subject.

Example 18: The system of any one of examples 13-17, where the second wavelength, $\lambda_2$, is a wavelength in a range of 425 nm to 475 nm, and where the analyte is bilirubin.

Example 19: The system of any one of examples 13-18, where the first wavelength, $\lambda_1$, is a wavelength in a range of 480 nm to 520 nm, where the second wavelength, $\lambda_2$, is a wavelength in a range of 425 nm to 475 nm, and where the analyte is bilirubin.

Example 20: The system of any one of examples 13-19, where providing, at the first time, light having the first wavelength, $\lambda_1$, to the subject, includes providing a continuous spectrum of light having a wavelength within a range of 480 nm and 520 nm to the subject at the first time, where providing, at the second time, light having the first wavelength, $\lambda_1$, to the subject, includes providing a continuous spectrum of light having a wavelength within a range of 480 nm and 520 nm to the subject at the second time, where the second wavelength, $\lambda_2$, is a wavelength in a range of 425 nm to 475 nm, and where the analyte is bilirubin.

Example 21: The system of any one of examples 13-20, where providing, at a first time, light having the first wavelength, $\lambda_1$, to the subject includes providing the light having the first wavelength to a first location of a surface of the subject, where providing, at a second time, light having the first wavelength, $\lambda_1$, to the subject includes providing the light having the first wavelength to the first location of the surface of the subject, where the detected light reflected from the subject in response to the light provided to the subject at the first time and at the second time is received from a plurality of second locations of the surface of the subject, where each of the second locations is a different distance from the first location, and where the computing device is further configured for determining concentrations of the analyte at different depths in the subject based on differences between the second amount of light reflected from the subject and the first amount of light reflected from the subject for the different distances between the first location and each of the second distances.

Example 22: The system of any one of examples 13-21, where determining the first amount of light reflected from the subject in response to the light provided at the first time includes determining a first reflectivity of the subject at the first time, where determining the second amount of light reflected from the subject in response to the light provided at the second time includes determining a second reflectivity of the subject at the second time, and where determining the concentration of the analyte in the subject includes determining the concentration based on a difference between the first reflectivity and the second reflectivity.

Example 23: The system of any one of examples 13-22, where the first light source is configured for providing light having the first wavelength to the subject in a first spot size on the subject and where the second light source is configured for providing light having the second wavelength to the subject in a second spot size on the subject, where the first spot size is greater than or equal to the second spot size.

Example 24: The method of any one of examples 13-23, where the light having the first wavelength, $\lambda_1$, and the light having the second wavelength, $\lambda_2$, is provided continuously to the subject and simultaneously is provided continuously to the subject for a time period of at least five seconds.

Some of the above example implementations are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed but may also have additional steps not included in the figure. The processes may correspond to methods, functions, procedures, subroutines, subprograms, etc.

Methods discussed above, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a storage medium. A processor(s) may perform the necessary tasks.

Specific structural and functional details disclosed herein are merely representative for purposes of describing example implementations. Example implementations, however, be embodied in many alternate forms and should not be construed as limited to only the implementations set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example implementations. As used herein, the term and/or includes any and all combinations of one or more of the associated listed items.

The terminology used herein is for the purpose of describing particular implementations only and is not intended to be limiting of example implementations. As used herein, the singular forms a, an, and the are intended to include the plural forms as well, unless the context clearly indicates otherwise. It will be further understood that the terms comprises, comprising, includes and/or including, when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example implementations belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the above example implementations and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the above illustrative implementations, reference to acts and symbolic representations of operations (e.g., in the form of flowcharts) that may be implemented as program modules or functional processes include routines, programs, objects, components, data structures, etc., that perform particular tasks or implement particular abstract data types and may be described and/or implemented using existing hardware at existing structural elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as processing or computing or calculating or determining of displaying or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example implementations are typically encoded on some form of non-transitory program storage medium or implemented over some type of transmission medium. The program storage medium may be magnetic (e.g., a floppy disk or a hard drive) or optical (e.g., a compact disk read only memory, or CD ROM), and may be read only or random access. Similarly, the transmission medium may be twisted wire pairs, coaxial cable, optical fiber, or some other suitable transmission medium known to the art. The example implementations not limited by these aspects of any given implementation.

Detailed implementations are disclosed herein. However, it is understood that the disclosed implementations are merely examples, which may be embodied in various forms. Therefore, specific structural and functional details disclosed herein are not to be interpreted as limiting, but merely as a basis for the claims and as a representative basis for teaching one skilled in the art to employ the implementations in virtually any appropriately detailed structure. Further, the terms and phrases used herein are not intended to be limiting, but to provide an understandable description of the present disclosure.

It should also be noted that whilst the accompanying claims set out particular combinations of features described herein, the scope of the present disclosure is not limited to the particular combinations hereafter claimed, but instead extends to encompass any combination of features or implementations herein disclosed irrespective of whether or not that particular combination has been specifically enumerated in the accompanying claims at this time. Additionally, while certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations.

What is claimed is:

1. A method of determining a concentration of analyte in a subject, the method comprising:

collecting light reflected from a subject in response to light having a first wavelength, $\lambda_1$, that is provided to the subject at a first time;

determining, based on the collected light, a first reflectivity of the subject in response to the light provided at the first time;

providing, over a period of time, light having a second wavelength, $\lambda_2$, that corresponds to an absorption wavelength of the analyte, wherein absorption of the second wavelength by the analyte causes a change of the reflectivity of the subject;

collecting light reflected from the subject in response to light having the first wavelength, $\lambda_1$, that is provided to the subject at a second time, wherein the second time is after the period of time;

determining, based on the collected light, a second reflectivity of the subject in response to the light provided at the second time;

determining the concentration of the analyte in the subject based on a difference between the second reflectivity and the first reflectivity.

2. The method of claim 1, wherein absorption of the light having the second wavelength by the analyte causes isomerization of the analyte in the subject.

3. The method of claim 1, wherein absorption of the light having the second wavelength by the analyte increases a solubility of the analyte in water.

4. The method of claim 1, further comprising:

determining a rate of change of a reflectivity of the subject during the period of time based on a difference between the second reflectivity and the first reflectivity; and determining the concentration based on the rate of change of the reflectivity of the subject.

5. The method of claim 1, wherein providing the light having the first wavelength includes providing the light having the first wavelength transcutaneously to the subject and wherein providing the light having the second wavelength includes providing the light having the second wavelength transcutaneously to the subject.

6. The method of claim 1, wherein the second wavelength, $\lambda_2$, is a wavelength in a range of 425 nm to 475 nm, and wherein the analyte is bilirubin.

7. The method of claim 1, wherein the first wavelength, $\lambda_1$, is a wavelength in a range of 480 nm to 520 nm, wherein the second wavelength, $\lambda_2$, is a wavelength in a range of 425 nm to 475 nm, and wherein the analyte is bilirubin.

8. The method of claim 1, wherein providing, at the first time, light having the first wavelength, $\lambda_1$, to the subject, includes providing a continuous spectrum of light having a wavelength within a range of 480 nm and 520 nm to the subject at the first time, wherein providing, at the second time, light having the first wavelength, $\lambda_1$, to the subject, includes providing a continuous spectrum of light having a wavelength within a range of 480 nm and 520 nm to the subject at the second time, wherein the second wavelength, $\lambda_2$, is a wavelength in a range of 425 nm to 475 nm, and wherein the analyte is bilirubin.

9. The method of claim 1, wherein providing, at a first time, light having the first wavelength, $\lambda_1$, to the subject includes providing the light having the first wavelength to a first location of a surface of the subject, wherein providing, at a second time, light having the first wavelength, $\lambda_1$, to the subject includes providing the light having the first wavelength to the first location of the surface of the subject, wherein collecting light reflected from the subject in response to the light provided to the subject at the first time and in response to the light provided to the subject at the first time includes collecting, at a plurality of second locations of the surface of the subject, the light reflected from the subject, wherein each of the second locations is a different distance from the first location, and further comprising:

determining concentrations of the analyte at different depths in the subject based on differences between the second reflectivity and the first reflectivity for the different distances between the first location and each of the second distances.

10. The method of claim 1, wherein determining the first reflectivity includes determining a first reflectivity of the subject at the first time, wherein determining the second reflectivity includes determining a second reflectivity of the subject at the second time, and wherein determining the concentration of the analyte in the subject includes determining the concentration based on a difference between the first reflectivity and the second reflectivity.

11. The method of claim 1, wherein a first spot size on the subject of the light having the first wavelength is greater than or equal to a second spot size on the subject of the light having the second wavelength.

12. The method of claim 1, wherein the light having the first wavelength, $\lambda_1$, and the light having the second wavelength, $\lambda_2$, is provided continuously to the subject and simultaneously is provided continuously to the subject for a time period of at least five seconds.

13. A system for determining a concentration of analyte in a subject, the system comprising:

a first light source configured for providing light having a first wavelength, $\lambda_1$, to the subject;

a second light source configured for providing light having a second wavelength, $\lambda_2$, that corresponds to an absorption wavelength of the analyte, wherein absorption of the second wavelength by the analyte causes a decrease of a reflectivity of the subject in response to the providing of light having the first wavelength;

a detector configured for detecting light reflected from the subject in response to the light provided to the subject;

a computing device configured for:

controlling the first light source to provide the light having the first wavelength, $\lambda_1$, to the subject at a first time and at a second time after the first time;

controlling the second light source to provide the light having the second wavelength, $\lambda_2$, to the subject over a period of time, wherein at least a portion of the period of time is after the first time and before the second time;

determining, based on the detected light, a first reflectivity of light reflected from the subject in response to the light provided at the first time;

determining, based on the detected light, a second reflectivity of light reflected from the subject in response to the light provided at the second time; and determining the concentration of the analyte in the subject based on a difference between the second reflectivity and the first reflectivity.

14. The system of claim 13, wherein absorption of the light having the second wavelength by the analyte causes isomerization of the analyte in the subject.

15. The system of claim 13, wherein absorption of the light having the second wavelength by the analyte increases a solubility of the analyte in water.

16. The system of claim 13, wherein the computing device is further configured for:

determining a rate of change of a reflectivity of the subject during the period of time based on a difference between the second reflectivity and the first reflectivity, and determining the concentration based on the rate of change of the reflectivity of the subject.

17. The system of claim 13, wherein providing the light having the first wavelength includes providing the light having the first wavelength transcutaneously to the subject and wherein providing the light having the second wavelength includes providing the light having the second wavelength transcutaneously to the subject.

18. The system of claim 13, wherein the second wavelength, $\lambda_2$, is a wavelength in a range of 425 nm to 475 nm, and wherein the analyte is bilirubin.

19. The system of claim 13, wherein the first wavelength, $\lambda_1$, is a wavelength in a range of 480 nm to 520 nm, wherein the second wavelength, $\lambda_2$, is a wavelength in a range of 425 nm to 475 nm, and wherein the analyte is bilirubin.

20. The system of claim 13, wherein providing, at the first time, light having the first wavelength, $\lambda_1$, to the subject, includes providing a continuous spectrum of light having a wavelength within a range of 480 nm and 520 nm to the subject at the first time, wherein providing, at the second time, light having the first wavelength, $\lambda_1$, to the subject, includes providing a continuous spectrum of light having a wavelength within a range of 480 nm and 520 nm to the subject at the second time, wherein the second wavelength, $\lambda_2$, is a wavelength in a range of 425 nm to 475 nm, and wherein the analyte is bilirubin.

21. The system of claim 13, wherein providing, at a first time, light having the first wavelength, $\lambda_1$, to the subject includes providing the light having the first wavelength to a first location of a surface of the subject, wherein providing, at a second time, light having the first wavelength, $\lambda_1$, to the subject includes providing the light having the first wavelength to the first location of the surface of the subject, wherein the detected light reflected from the subject in response to the light provided to the subject at the first time and at the second time is received from a plurality of second locations of the surface of the subject, wherein each of the second locations is a different distance from the first location, and wherein the computing device is further configured for determining concentrations of the analyte at different depths in the subject based on differences between the second reflectivity and the first reflectivity for the different distances between the first location and each of the second distances.

22. The system of claim 13, wherein includes determining the first reflectivity determining a first reflectivity of the subject at the first time, wherein determining the second reflectivity includes determining a second reflectivity of the subject at the second time, and wherein determining the concentration of the analyte in the subject includes determining the concentration based on a difference between the first reflectivity and the second reflectivity.

23. The system of claim 13, wherein the first light source is configured for providing light having the first wavelength to the subject in a first spot size on the subject and wherein the second light source is configured for providing light having the second wavelength to the subject in a second spot size on the subject, wherein the first spot size is greater than or equal to the second spot size.

24. The system of claim 13, wherein the light having the first wavelength, $\lambda_1$, and the light having the second wavelength, $\lambda_2$, is provided continuously to the subject and simultaneously is provided continuously to the subject for a time period of at least five seconds.

\* \* \* \* \*